United States Patent [19] [11] 4,167,061
Förster [45] Sep. 11, 1979

[54] ORTHODONTIC APPLIANCE

[75] Inventor: Rolf Förster, Pforzheim, Fed. Rep. of Germany

[73] Assignee: Bernhard Förster, Pforzheim, Fed. Rep. of Germany

[21] Appl. No.: 755,224

[22] Filed: Dec. 29, 1976

[30] Foreign Application Priority Data

May 28, 1976 [DE] Fed. Rep. of Germany ....... 2623943
Oct. 28, 1976 [DE] Fed. Rep. of Germany ....... 2648989

[51] Int. Cl.² .............................................. A61C 7/00
[52] U.S. Cl. .................................................. 32/14 D
[58] Field of Search ................................. 32/14 D, 20

[56] References Cited

U.S. PATENT DOCUMENTS

| | | | |
|---|---|---|---|
| 2,874,468 | 2/1959 | De Woskin | 32/14 D |
| 3,203,099 | 8/1965 | Interlandi | 32/14 D |
| 3,526,035 | 9/1970 | Armstrong | 32/14 D |
| 3,765,093 | 10/1973 | De Woskin | 32/14 D |
| 3,772,789 | 11/1973 | De Woskin | 32/14 D |
| 4,040,188 | 8/1977 | Masel | 32/14 D |

Primary Examiner—Russell R. Kinsey
Assistant Examiner—John J. Wilson

[57] ABSTRACT

This invention relates to an orthodontic appliance for correcting the positions of teeth in a jaw. Embodiments of the invention are provided with a low pull and/or a high pull and comprise adjustable spring or rubber elements for transmitting the correcting forces to the teeth. The spring or rubber elements are disposed on the outside of the mouth closely beside the teeth so that the latter are not subjected to disturbing turning and tilting torques. Turning movements of the head and movements of the jaw are compensated. A combination of a high pull and a low pull enables an optimum adjustment of the magnitude and direction of the correcting forces.

22 Claims, 8 Drawing Figures

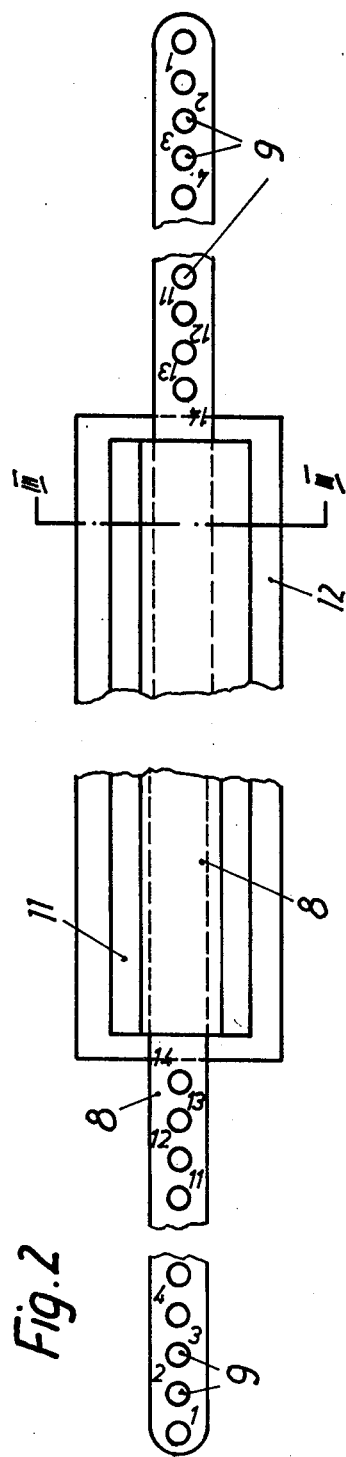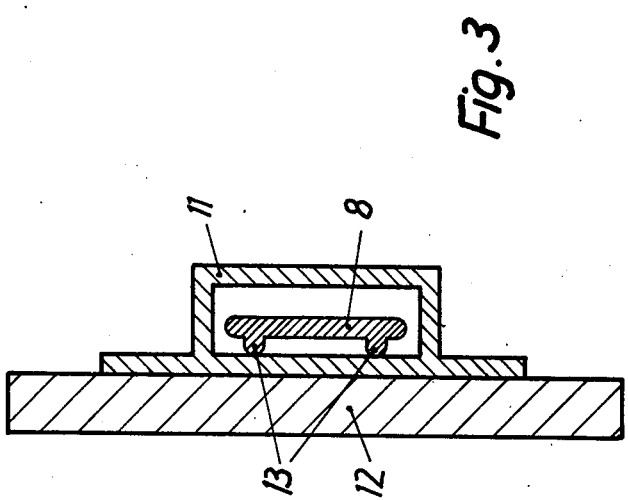

ORTHODONTIC APPLIANCE

SUMMARY OF THE INVENTION

This invention relates to an orthodontic appliance which comprises a low pull and/or a high pull and a face bow for transmitting tensile forces from spring or rubber elements to an oral tooth-jaw bow, which is connected to the (molar) teeth to be corrected.

In various known oral and extra-oral orthodontic methods, the teeth to be corrected are acted upon by straps. For instance, the orthodontic appliance disclosed in German Patent Specification 110,996 comprises an extra-oral face bow, which extends over the cheeks of the patient and is provided at each end, approximately on the ear level, with a hook for connection to an elastic low pull. An oral tooth-jaw bow is welded to the face bow near the lips. The ends of the oral bow are connected by straps to the molar teeth to be corrected. The elastic low pull is subject to fatigue in use and must be replaced or readjusted after a certain time of use. The forces applied cannot be exactly adjusted.

Opened German Specification No. 1,964,207 and Printed German Application No. 2,233,393 disclose arrangements in which springs are incorporated in the low pull near the ends thereof and the tensile force exerted by said springs can be adjusted and maintained constant. On the other hand, it is inherent in that design that the face bow extends as far as to the ear region so that the molar teeth to be corrected are acted upon by a force on a line which is much behind the ear region and the anatomy of the head, particularly the face angle, results in an additional lever arm and in additional torques on the means connected to the molar teeth to be corrected so that the latter are subjected to undesired torques about vertical and horizontal axes. Another disadvantage of these known orthodontic appliances resides in that a movement of the head results in a higher tension on one side than on the other so that the teeth may not be properly corrected by this appliance, which is mainly worn by the patient when he is asleep and does not hold his head straight.

It is an object of the invention to provide an orthodontic appliance which does not exert undesired turning and tilting torques on the (molar) teeth to be corrected and regardless of its adjustment does not exert different tensile forces on the teeth to be corrected so that these will not be subjected to asymmetrical correcting forces even when the head is turned aside or downward or upward.

Another object of the invention is to enable an adjustment of an optimum direction of the correcting forces.

In one embodiment of the invention, the orthodontic appliance comprises an oral bow provided with means for connection to the teeth (molar teeth) to be corrected, two extra-oral face bow portions, which are joined to the oral bow, a low pull, which is adjustable in length, and spring or rubber elements extending substantially parallel to the means for connection to the molar teeth and connecting said low pull to the free ends of the face bow portions. Particularly when spring elements are used, the appliance comprises a scale and means for indicating the spring tension on said scale.

Rubber elements may consist of removably mounted rubber rings which differ in size and elasticity. Spring elements consist suitably of a tension spring in a housing, which is provided with said scale.

A spring element may be integrally or detachably joined to each face bow portion. The low pull may be provided in each of its opposite end portions with a series of holes, and the housing of each spring element may be provided at its rear end with a hook which can be hooked into one of said holes so that the spring tension can be adjusted by the selection of the hole into which the hook is hooked. This arrangement will avoid the occurrence of a torque about a vertical or horizontal axis when the head is turned aside.

The low pull extends in a guide sleeve, which is provided with a fabric covering for engaging the nape of the neck of the wearer. In a preferred arrangement, the low pull is provided with a pair of low-friction slide rails contained in the guide sleeve, and the low pull contacts the guide sleeve only at the two low-friction slide rails, a lateral turning of the head will not result in an action of different tensile forces on the molar teeth to be corrected because the low pull will move entirely in unison with the head as it is turned aside.

In another embodiment of the invention, the orthodontic appliance comprises an oral bow provided with means for connection to the teeth (molar teeth) to be corrected, two extra-oral face bow portions, which are joined to said inner bow, a high pull, which is adjustable in length and adapted to extend around the back of the head, and spring or rubber elements connected to the high pull and to the free ends of the face bow portions by articulated joints. Particularly when spring elements are used, the appliance comprises a scale and means for indicating the spring tension on said scale.

In the embodiment comprising a high pull, the forces acting on the molar teeth will not be changed when the head is turned aside or upward or downward, and whereas jaw movements may change the direction of the forces this will be compensated in accordance with the invention by the articulated joints connecting the spring elements to the ends of the high pull and to the free ends of the face bow portions.

In a preferred embodiment, each spring element is provided at both ends with respective hooks, one of which is adapted to be hooked into an eyelet or other hook-engaging means provided at the rear end of face bow portions and the other of which is adapted to be hooked into one of a series of holes in the adjacent end portion of the high pull so that the spring tension can be adjusted by a selection of the hole into which the hook is hooked.

In a preferred embodiment, the orthodontic appliance comprises both a high pull and a low pull, each of which is provided in its end portions with a series of holes, and each spring element is connected at one end to one end of the high pull and to one end of the low pull. Such orthodontic appliance permits of an adjustment of an optimum direction of the force required for an effective tooth correction. In the practice of this appliance, a radiogram of the teeth to be corrected is made and is used to determine the lines of action of the forces required for the correction. The hooks carried by the spring elements of the orhodontic appliance are then hooked into such holes in the low pull and high pull that the low pull and high pull intersect on the lines of force action which have been determined.

SHORT DESCRIPTION OF THE DRAWINGS

FIG. 2 is a diagrammatic elevation showing the low pull of FIG. 1.

FIG. 3 is an enlarged transverse sectional view taken on line III—III in FIG. 2 and showing the low pull.

DETAILED DESCRIPTION OF THE DRAWINGS

Figure 1:
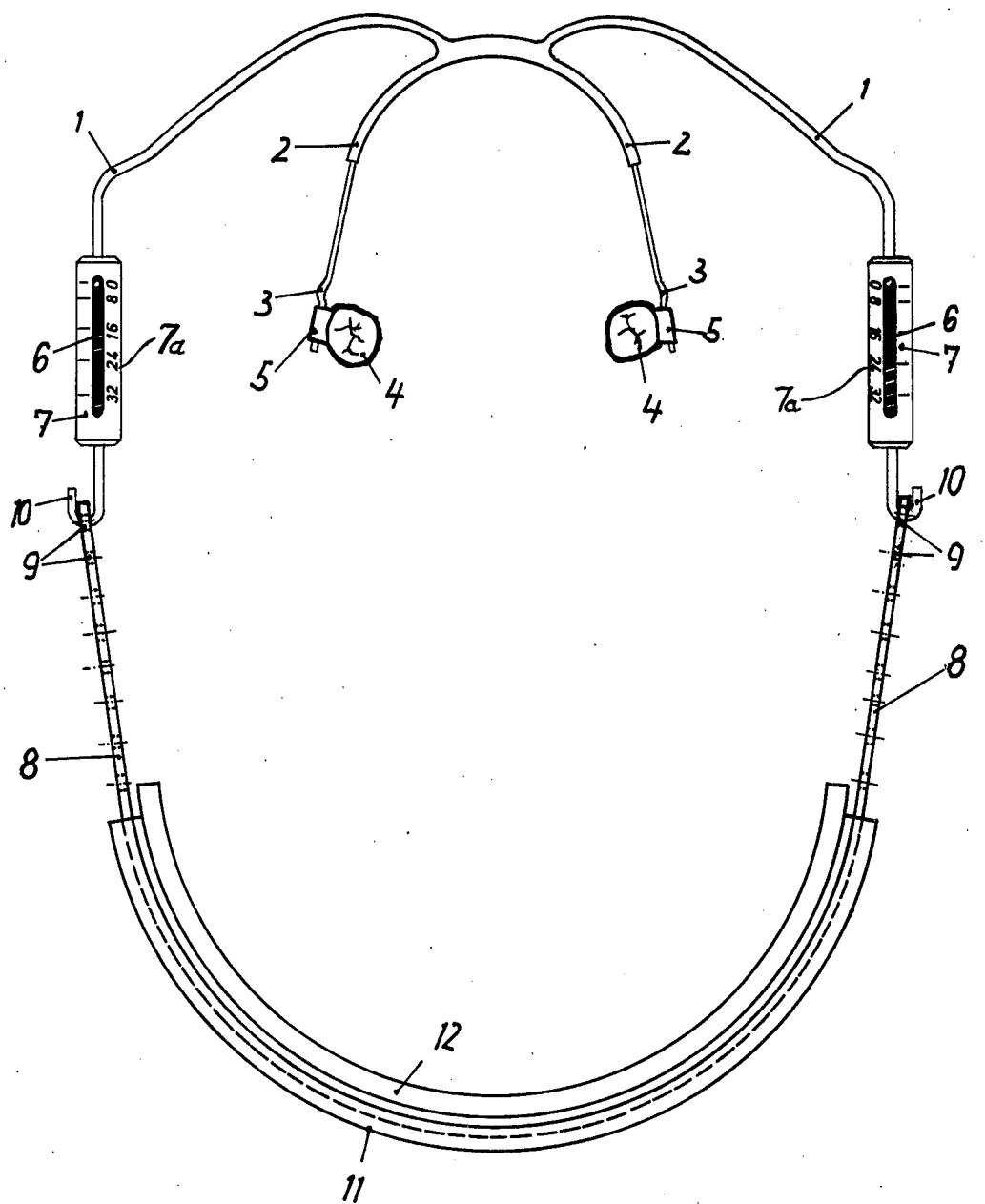
FIG. 1 is an elevation showing face bow portions and an inner bow of an orthodontic appliance comprising a low pull and spring elements integrally joined to the face bow portions.

FIG. 1 shows an orthodontic appliance comprising two extra-oral face bow portions 1, which are joined to an oral tooth-jaw bow 2, which is provided with force-exerting means 3 for connection by respective straps 5 to the molar teeth 4 to be connected. Each face bow portion 1 is provided at its free end with a spring element which comprises a tension spring 6 contained in a housing 7, which is provided with a tension-indicating scale 7a. Each spring element 6, 7 can be adjustably connected to a low pull 8 by a hook 10 carried by the spring element and holes 9 in the low pull.

Figure 1A:
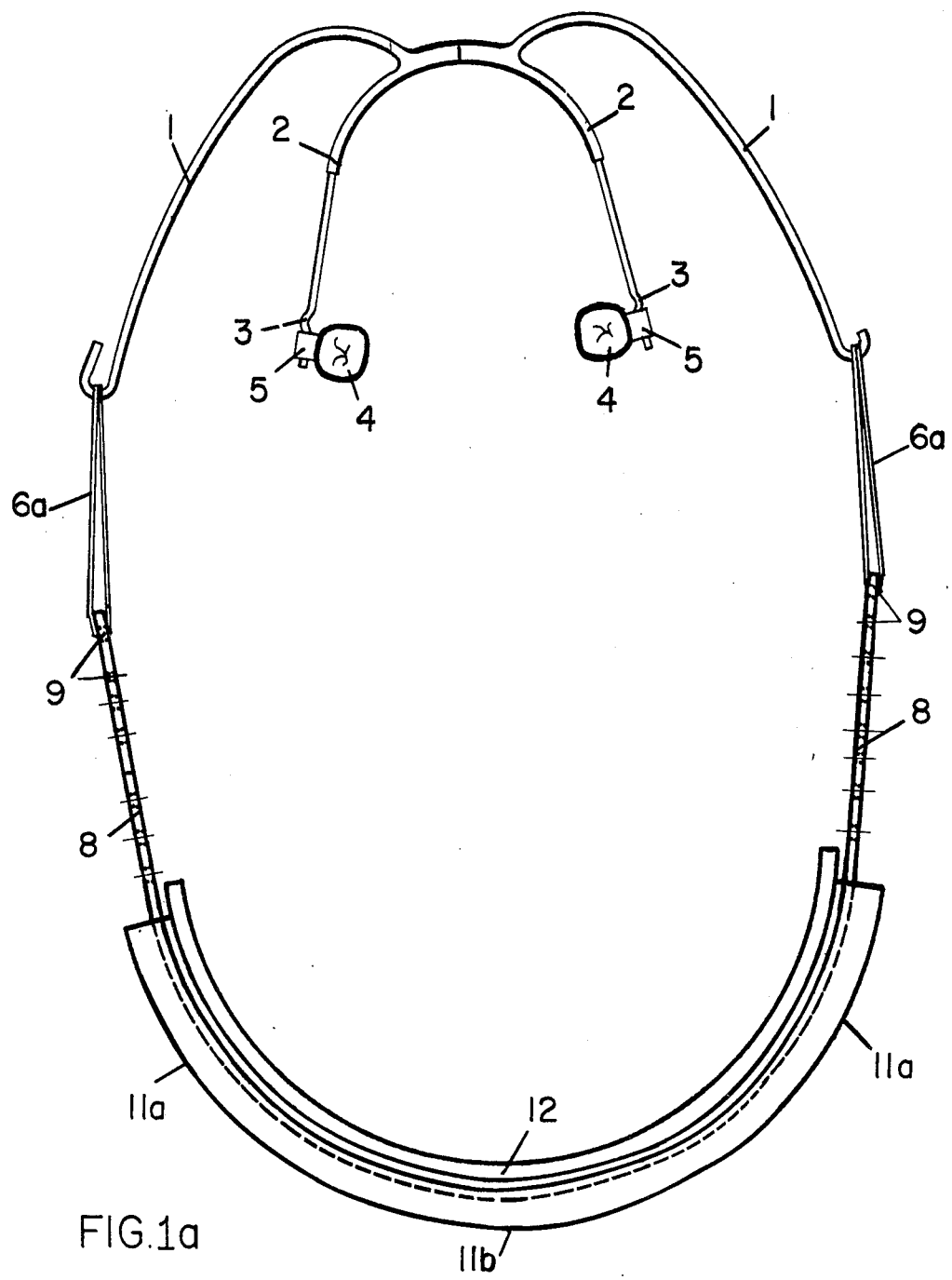
FIG. 1a is an elevation showing face bow portions and an inner bow of an orthodontic appliance comprising a low pull and rubber elements detachably mounted or connected to the face bow portions.

FIG. 1a shows rubber elements or rings 6a detachably mounted or connected to bow portions 1.

FIGS. 2 and 3 show that the low pull 8 extends in a guide sleeve 11, which has a fabric covering 12 for engaging the nape of the neck of the patient.

The low pull 8 has two slide rails 13, which consist of two projections extending along the length of the low pull, and is provided in each end portion with a series of holes 9 to which a spring element 6, 7 carried by a face bow portion 1 can be adjustably connected by its hook 10.

Because the spring elements are integrally joined to the face bow portions and extend approximately parallel to the force-exerting means of the inner bow portion, the occurrence of a torque about a vertical or horizontal axis, which would adversely affect the correcting action on the teeth, is avoided. The slidable mounting of the low pull ensures that the tensile forces acting on the molar teeth to be corrected will not be changed when the patient turns his head aside, e.g., when he is asleep.

Figure 4:
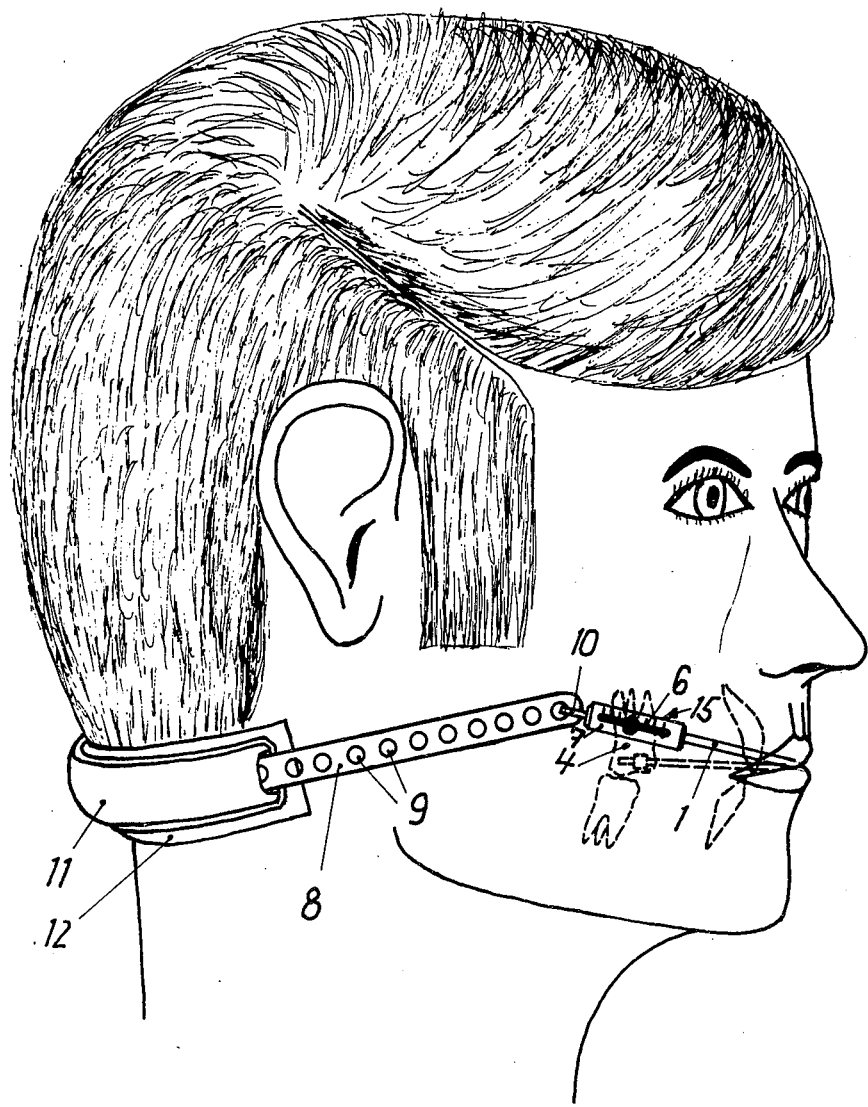
FIG. 4 shows an orthodontic appliance comprising a low pull and applied to the head of a patient.

It is apparent from FIG. 4 how the orthodontic appliance shown in FIGS. 1 to 3 is applied to the head of a patient. It is shown that each spring element 15 comprises a housing 7, which contains a tension spring 6, which is connected to the hook 10 that extends out of the housing 7, and that the spring elements 15 are disposed on the outside of the face beside the teeth 4 to be corrected and extend approximately parallel to the force-exerting means 3 connected to the straps 5 (FIG. 1).

Figure 5:
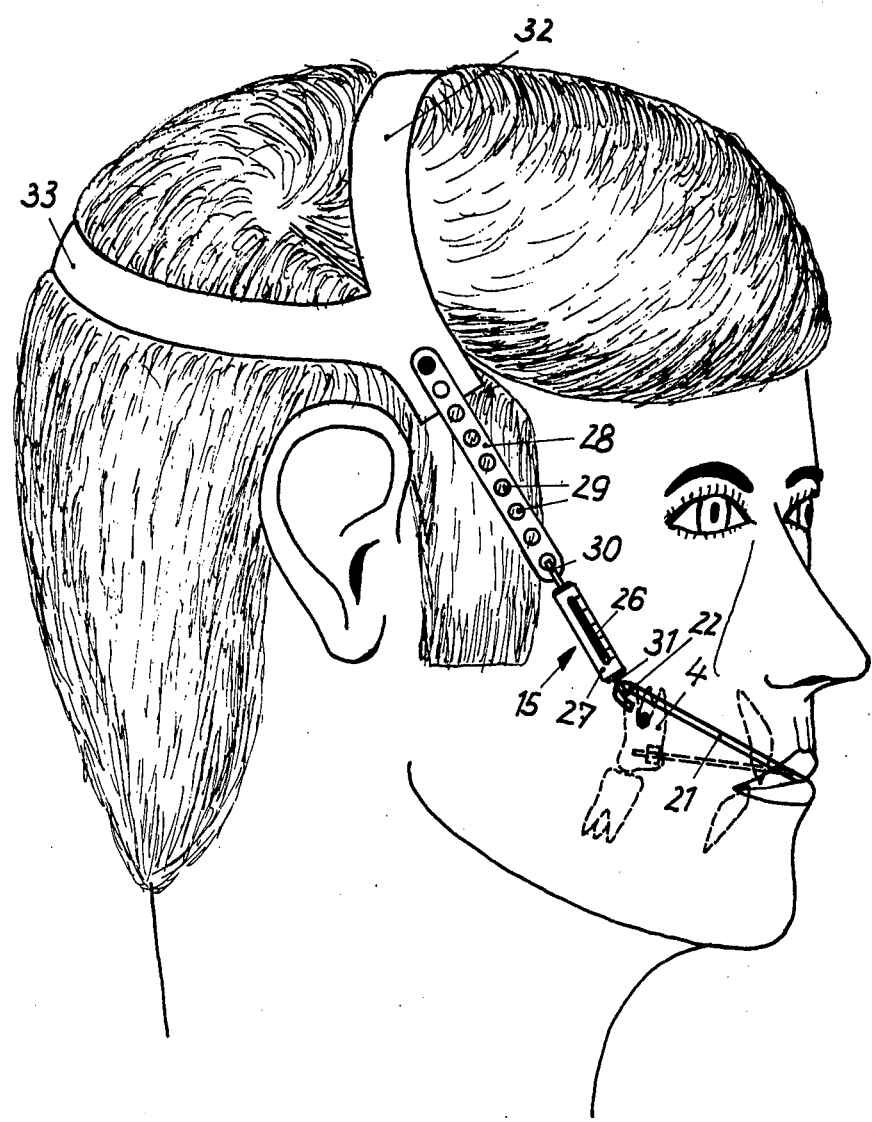
FIG. 5 shows an orthodentic appliance comprising a high pull and applied to the head of a patient.

In the orthodontic appliance shown in FIG. 5, the outer face bow portions 21 are connected to a high pull 28 by spring elements 15, which comprise a housing 27 and a tension spring 26 contained in the housing. Each spring element 15 is connected to the high pull 28 and to the free end of the adjacent face bow portion 21 by articulated joints comprising a forward hook 31 carried by the housing and connected to the face bow portion 21 and a rear hook 30 which is fixed to the spring 26 and connected to the high pull 28. The high pull comprises two straps 32 and 33, which extend around the back of the patient's head and are reliably held there. Each end portion of the high pull 28 is provided with a series of holes 29. In dependence on the desired correcting force to be applied, the rear hook 30 of each spring element 15 is hooked into one of the holes 29 at the adjacent end of the high pull. The forward hooks 31 of the spring elements 15 are hooked into hooks 22 or eyelets at the free ends of the face bow portions 21. In the embodiment shown in FIG. 5 the spring elements 15 are also disposed close to the teeth 4 to be corrected, which are subjected in this case to a tensile force acting in an upwardly inclined direction. The articulated joints connecting the spring elements 15 ensure that a movement of the jaws will not result in a change of the direction of force action.

Figure 6:
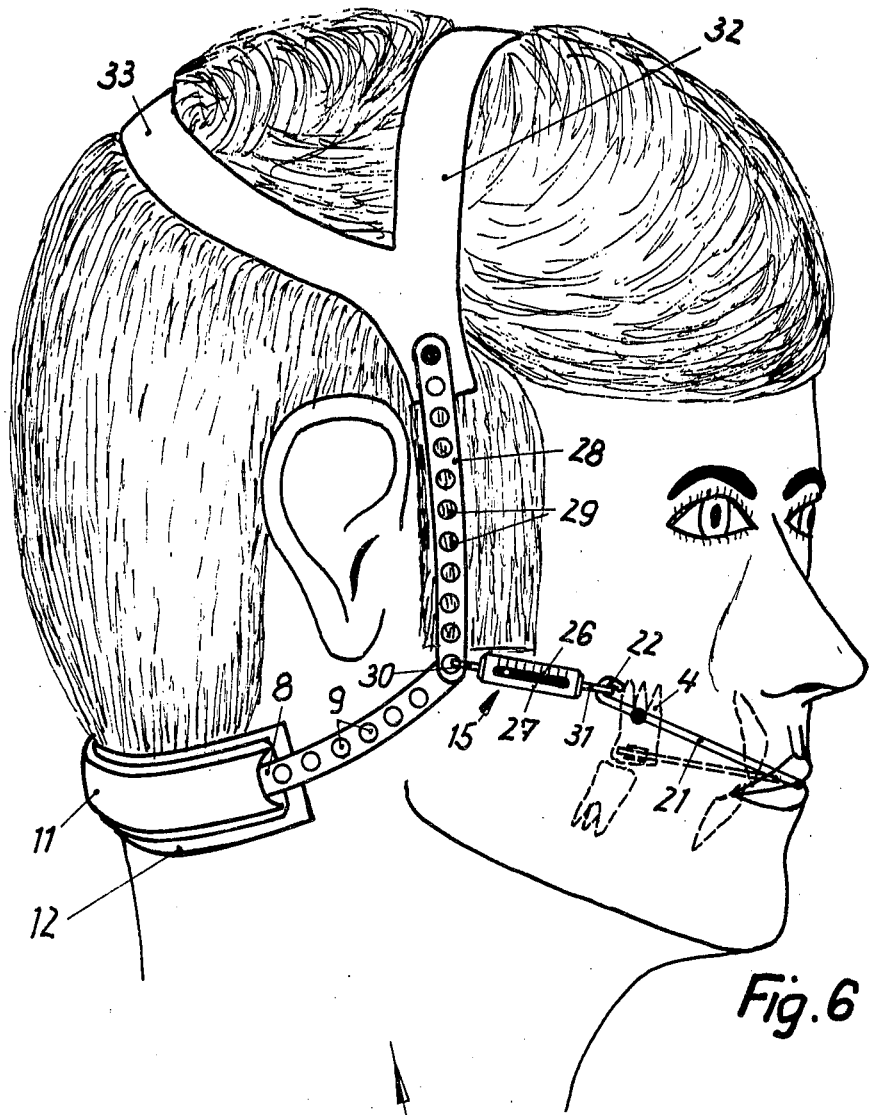
FIG. 6 shows an orthodontic appliance comprising a combination pull and applied to the head of a patient.

FIG. 6 shows an orthodontic appliance which comprises a high pull 28 and a low pull 8. The low pull 8 shown in FIGS. 1 to 4 has been added to the orthodontic appliance shown in FIG. 5. This orthodontic appliance comprising a combination pull permits of an optimum adjustment of the magnitude and direction of the correcting forces in that the hook 30 at the rear end of each spring element 15 is hooked into holes 9 and 29 at the same time and such holes 9 and 29 are selected so that the low pull 8 and the high pull 28 intersect on the line of action of a force having the predetermined magnitude.

Figure 7:
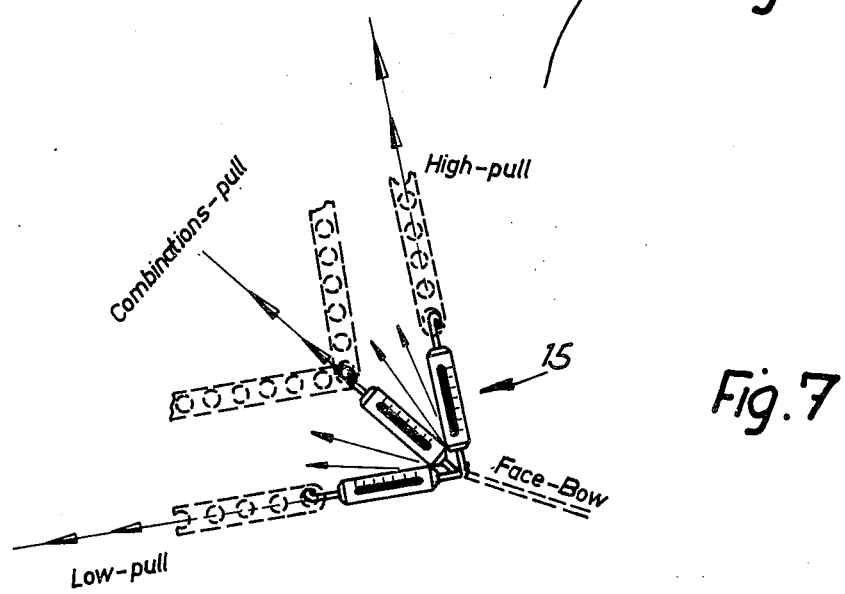
FIG. 7 is a diagrammatic view illustrating directions of lines of action of correcting forces which can be exerted by the orthodontic appliances shown in FIGS. 4, 5, and 6.

With such orthodontic appliance, the optimum direction of force action for the desired tooth correction can be adjusted in the manner illustrated in FIG. 7. A radiogram of the teeth to be corrected is made first and is used to determine the line of action of the force required for the correction. The hooks of the spring elements of the orthodontic appliance are then hooked in such holes of the low pull and the high pull that the low pull and high pull intersect on the lines of force action which have been determined. To that end, each hook 30 is hooked into holes 9 and 29 which lie on said line of force action when the appliance is properly applied to the head of the wearer.

What is claimed is:

1. An orthodontic appliance comprising
an oral bow provided on opposite sides with force-applying portions adapted to be connected to teeth to be corrected,
two extra-oral face bow portions joined to said oral bow and having free ends on opposite sides of said oral bow,
a low pull having two terminal portions at opposite ends thereof and at least one slide rail, said terminal portions being disposed on opposite sides of the head of the patient, said slide rail being a projection extending along the length of the low pull,
two resilient elements, each of which is connected between one of said free ends and one of said terminal portions, said resilient elements extending substantially parallel to said force-applying portions when the latter are connected to at least one tooth to be corrected, tension-adjusting means for changing the effective length of said low pull, and a guide sleeve through which said low pull extends, said sleeve arranged to engage the nape of the neck of the patient when said low pull is applied, said slide rail being contained in said guide sleeve, and said low pull contacts said guide sleeve only at said slide rail, so that said low pull will move entirely in unison with the head as it is turned aside and the occurrence of undesirable torques affecting the teeth to be corrected is substantially avoided.

2. An orthodontic appliance as set forth in claim 1, in which said force-applying means are adapted to be connected to molar teeth to be corrected.

3. An orthodontic appliance as set forth in claim 1, in which said resilient elements comprise rubber elements.

4. An orthodontic appliance as set forth in claim 3, in which said rubber elements comprise detachably mounted rubber rings.

5. An orthodontic appliance as set forth in claim 4, in which said rubber rings are selected from a set of rubber rings which differ in size and elasticity.

6. An orthodontic appliance as set forth in claim 1, in which each of said resilient elements is detachably connected to one of said face bow portions and one of said terminal portions.

7. An orthodontic appliance as set forth in claim 1, in which said resilient elements comprise spring elements.

8. An orthodontic appliance as set forth in claim 7, in which
each of said spring elements comprises a housing and a tension spring contained in said housing, and
said housing is provided with a scale for indicating the tensile force exerted by said spring.

9. An orthodontic appliance as set forth in claim 7, in which
each of said spring elements comprises a housing and a tension spring contained in said housing, and
said housing is provided with a scale for indicating the tensile force exerted by said spring.

10. An orthodontic appliance as set forth in claim 1, wherein said guide sleeve is provided with a fabric covering arranged to engage the nape of the neck of the patient when said low pull is applied.

11. An orthodontic appliance as set forth in claim 1, in which said resilient elements are integrally joined to said face bow portions.

12. An orthodontic appliance as set forth in claim 1, in which said adjusting means comprise a series of holes formed in each of said terminal portions and spaced apart along the same and
two hooks are carried by respective ones of said resilient elements and hooked each in a selected one of said holes in one of said terminal portions.

13. An orthodontic appliance as set forth in claim 1, in which said low pull is provided with two slide rails being two projections extending along the length of said low pull.

14. An orthodontic appliance comprising
an oral bow provided on opposite sides with force-applying portions adapted to be connected to teeth to be corrected,
two extra-oral face bow portions joined to said oral bow and having free ends on opposite sides of said oral bow,
a low pull having two first terminal portions at opposite ends thereof, and at least one slide rail,
a guide sleeve through which said low pull extends, said sleeve arranged to engage the nape of the neck of the patient when said low pull is applied,
said slide rail being a projection extending along the length of said low pull and contained in said guide sleeve, said low pull contacts said guide sleeve only at said slide rail,
a high pull having two second terminal portions at opposite ends thereof,
two resilient elements, each of which is connected at one end to one of said first terminal portions,
articulated joints connecting each of said resilient elements at said one end to one of said second terminal portions, and at its opposite end to one of said free ends, and
tension-adjusting means for changing the effective lengths of said low pull and said high pull,
said low pull and high pull being adapted to be applied to a patient to extend around the nape of his neck and around his head, respectively, in such a manner that said first terminal portions as well as said second terminal portions are disposed on opposite sides of the head of the patient, and said resilient elements extend generally parallel to said force-applying portions when the latter are connected to at least one tooth to be corrected.

15. An orthodontic appliance as set forth in claim 14, in which
said tension-adjusting means comprise a series of holes formed in each of said terminal portions and spaced apart along the same and
said articulated joints comprise two hooks carried by respective ones of said holes in one of said first terminal portions and a selected one of said holes in one of said second terminal portions.

16. An orthodontic appliance as set forth in claim 14, wherein said guide sleeve is provided with a fabric covering arranged to engage the nape of the neck of the patient when said low pull is applied.

17. An orthodontic appliance as set forth in claim 16, in which
said low pull is provided with two slide rails being two projections extending along the length of said low pull and said low pull contacts said guide sleeve only at said slide rails.

18. An orthodontic appliance as set forth in claim 14, further comprising a plurality of resilient elements, at least two of which are connected between one of said free ends and one each of said first terminal portions and said second terminal portions.

19. An orthodontic appliance as set forth in claim 14, in which said articulated joints comprise two hooks provided at opposite ends of each of said resilient elements and hook-retaining means provided at said free ends and said terminal portions and interlocking with said hooks.

20. An orthodontic appliance as set forth in claim 19, in which each of said resilient elements comprises
a housing provided with a hook interlocking with said hook-retaining means provided at one of said free ends and
a tension spring contained in said housing and provided with a hook interlocking with said hook-retaining means provided at one of said terminal portions.

21. An orthodontic appliance as set forth in claim 20, in which said tension adjusting means comprise a series of holes formed in each of said terminal portions and spaced apart along the same and adapted to constitute one of said hook-retaining means.

22. An orthodontic appliance as set forth in claim 19, in which said tension adjusting means comprise a series of holes formed in each of said terminal portions and spaced apart along the same and adapted to constitute one of said hook-retaining means.

* * * * *